US005637324A

United States Patent [19]
Bland

[11] Patent Number: 5,637,324
[45] Date of Patent: Jun. 10, 1997

[54] MEDICAL FOOD COMPOSITION FOR METABOLIC DETOXIFICATION

[76] Inventor: Jeffrey S. Bland, 957 11th La., Fox Island, Wash. 98333

[21] Appl. No.: 463,628

[22] Filed: Jun. 6, 1995

Related U.S. Application Data

[62] Division of Ser. No. 156,090, Nov. 22, 1993, which is a continuation of Ser. No. 815,290, Dec. 31, 1991, abandoned.

[51] Int. Cl.$^6$ .................. A61K 31/19; A61K 31/195; A61K 31/23; A61K 31/28; A61K 33/06; A61K 33/24; A61K 38/00; A61K 38/02

[52] U.S. Cl. .................. 424/655; 424/195.1; 424/600; 424/601; 424/617; 424/639; 424/641; 424/646; 424/656; 424/678; 424/682; 424/702; 514/2; 514/7; 514/12; 514/23; 514/24; 514/25; 514/42; 514/53; 514/54; 514/62; 514/184; 514/332; 514/355; 514/356; 514/387; 514/458; 514/474; 514/492; 514/494; 514/502; 514/505; 514/547; 514/554; 514/556; 514/557; 514/558; 514/560; 514/561; 514/562; 514/574; 514/655; 514/725; 514/763; 514/904; 514/905

[58] Field of Search ............... 424/617, 678, 424/681, 682, 655, 195.1, 600, 601, 639, 641, 646, 656, 702; 426/73, 74, 618; 514/2, 23, 53, 54, 7, 12, 24, 25, 42, 62, 184, 332, 355, 356, 387, 458, 474, 492, 494, 502, 505, 547, 554, 556, 557, 558, 560–562, 574, 655, 725, 763, 904, 905

[56] References Cited

U.S. PATENT DOCUMENTS

| | | | |
|---|---|---|---|
| 2,283,817 | 5/1942 | Martin et al. | 514/255 |
| 3,697,287 | 10/1972 | Winitz | 426/73 |
| 3,925,568 | 12/1975 | Rao et al. | 426/618 |
| 3,952,115 | 4/1976 | Damico et al. | 426/618 |
| 4,009,265 | 2/1977 | Howard | 514/21 |
| 4,112,123 | 9/1978 | Roberts | 426/656 |
| 4,582,705 | 4/1986 | Primes et al. | 424/632 |
| 4,582,801 | 4/1986 | Hamada et al. | 435/71.1 |
| 4,619,831 | 10/1986 | Sharma | 426/93 |
| 4,639,420 | 1/1987 | Schaffner | 435/7.1 |
| 4,849,225 | 7/1989 | Mitsuhashi et al. | 426/618 |
| 4,876,096 | 10/1989 | Mictchell et al. | 426/618 |
| 5,132,113 | 7/1992 | Luca | 426/72 |
| 5,358,933 | 10/1994 | Porro | 514/15 |
| 5,587,399 | 12/1996 | Acosta et al. | 514/561 |

OTHER PUBLICATIONS

I.M. Cox, et al., The Lancet, "Red Blood Cell Magnesium and Chronic Fatigue", vol. 337, Mar. 30, 1991, pp. 757–760, (p. 757 only).

Adrian Hunnisett, et al., Journal of Nutritional Medicine, "Gut Fermentation (or the 'Auto–brewery') Syndrome: a New Clinical Test with Initial Observations and Discussion of Clinical Test with Initial Observations and Discussion of Clinical and Biochemical Implications", 1990, pp. 33–38, (p. 33 only).

H. Malchow, et al., "Feasibility and Effectiveness of a Defined–Formula Diet Regimen in Treating Active Crohn's Disease", one page, (No Date Available).

Don M. Tucker, et al., Am. J. Clin. Nutr., "Nutrition Status and Brain Function in Aging[1,2]", 1990, vol. 52, pp. 93–102, (p. 93 only).

Jens Kjeldsen–Kragh, et al., The Lancet, "Controlled Trial of Fasting and One–Year Vegetarian Diet in Rheumatoid Arthritis", 1991, vol. 338, No. 8772, pp. 899–902, (first page only).

Frank Edward Allen, The Wall Street Journal, "Lonely Crusade: One Man's Suffering Spurs Doctors to Probe Pesticide–Drug Link", Monday, Oct. 14, 1991, Page one and p. A4, col. 1.

Smith Kline & French, Product Information, "Tagamet", pp. 2120, 2121, (No Publication Date Available).

Kaye H. Kilburn, M.D., "Neurobehavioral Dysfunction in Firemen Exposed to Polychlorinated Biphenyls (PCBs): Possible Improvement after Detoxification", Nov./Dec. 1989, vol. 44, No. 6, p. 345 (first page only).

John T. Sword, et al., American Institute of Nutrition, "Endotoxin and Lipid Peroxidation In Vivo in Selenium– and Vitamin E–Deficient and –Adequate Rats[1,2]", 1991, p. 251 only.

A.D. Thomson, FRCP(ed). Ph.d , et al., Am J Clin Nutr, "Possible Role of Toxins In Nutritional Deficiency[1]" 1987, vol. 45, pp. 1351–1360 (p. 1351 only).

Brian Ketterer, et al., Environmental Health Perspectives, "The Role of Glutathione in Detoxication", 1983, vol. 49, pp. 59–69 (first page only).

Compendium of Drug Therapy, New York, Biomedical Information Corp., 1983, pp. 47:50–47:72.

Martindale THE Extra Pharmacopoeia, 28th ed. London, The Pharmaceutical Press, 1982, pp. 47–48.

Remington's Pharmaceutical Sciences, 16th ed. Easton (PA), Mack Publishing Co., 1980, pp. 945–947, 970–971, 973–975, and 803.

The Merek Index, 10th edition, Rahway (NJ), Merk & Co., Inc. 1983, p. 1197.

Primary Examiner—John Pak
Attorney, Agent, or Firm—Klein & Szekeres, LLP

[57] ABSTRACT

A medical food having the below listed components is administered for several days as the sole source or as a substantial source of the daily caloric intake of a patient suffering from metabolic poisoning: 45 to 65% protein concentrate; 2.5 to 17.5% of grain syrup solids containing 50% dextran; 2.5 to 17.5% of grain syrup solids containing 50% of maltose; 3 to 12% of oil containing 20% of oleic acid, 1 to 11% medium chain triglycerides; magnesium ions; buffering agent; soluble calcium salt; ascorbic acid; 0.40 to 0.65% of β carotene; D-α-tocopherol; chromium ions in the trivalent or hexavalent form, 0.008 to 0.022% glutathione, 0.08 to 0.22% N-acetylcysteine; L-lysine hydrochloride; 0.08 to 0.22% L-threonine, and 0.08 to 0.22% of L-cysteine.

12 Claims, No Drawings

MEDICAL FOOD COMPOSITION FOR METABOLIC DETOXIFICATION

CROSS-REFERENCE TO RELATED APPLICATIONS

This is a divisional of application Ser. No. 08/156,090 filed on Nov. 22, 1993, which is a continuation of application Ser. No. 07/815,290, filed on Dec. 31, 1991, now abandoned.

BACKGROUND OF THE INVENTION

1. Field of the Invention

The present invention is in the field of medical foods. More particularly, the present invention is directed to a composition of an enteral nutrition product, which when taken alone, or in combination with certain conventional food sources, helps to upregulate hepatic detoxification enzyme systems thereby reducing the symptoms associated with endotoxicity and exotoxicity.

2. Brief Description of the Prior Art

Compositions containing vitamins, essential fatty acids, amino acids and related nutritional supplements are well known in the art. Nutritional formulas designed to provide a reasonably balanced diet while causing weight loss in persons who desire such weight loss, are also known in the art. Moreover, the nutritional role, and on a molecular level, the biochemical mode of action of most vitamins, amino acids, fatty acids, carbohydrates and other nutritionally active compounds and compositions have been extensively investigated in the prior art and are described in voluminous scientific and medical literature.

Many persons suffer chronic symptoms of toxicity associated with unidentified environmental or metabolic causes. These symptoms include fatigue, hypotonia, depression, lassitude, muscle weakness, insomnia, recurring bad dreams, intestinal complaints, myalgia, confusion, and functional nervous system problems. The term "metabolic poisoning" which has been accepted in the medical arts, refers to buildup within cells, tissues and organs of non-end product metabolites which alter the pH gradient and electrolyte balance within a cell, or which serve as enzyme inhibitors and which adversely affect the functioning of cells, and lead to one or more of the above-noted symptoms.

Whereas specific drugs, vitamins and nutritional supplements have been known and used in the prior art as antidotes for specific poisons, as anti-allergy drugs, and to remedy vitamin and other nutritional deficiencies, as far as the present inventor is aware the prior art has not provided any medical food which specifically facilitates up regulation of hepatic detoxication systems thereby accelerating the clearance of endo or exotoxins from persons suffering from metabolic poisoning. The present invention provides such a product and thereby provides a remedy for persons with lowered hepatic detoxification ability.

SUMMARY OF THE INVENTION

It is an object of the present invention to provide a dietary composition, which when taken alone or in combination with certain conventional food sources, stimulates the action of enzymes which are capable of removing undesired accumulated non-end product metabolites from the human body, and which product, as a result of said increased enzyme activity, substantially increases the rate of clearance from the body of accumulated undesired non-end-product metabolites and toxins.

The foregoing and other objects of the present invention are attained by administering to a human being who suffers from chronic non-end product metabolite accumulation (metabolic poisoning) a diet, wherein a substantial portion of the persons caloric intake is a composition comprising at least the following ingredients:

approximately 45 to 65 percent by weight of a protein concentrate selected from a group consisting of grain protein concentrate and vegetable protein concentrate;

approximately 2.5 to 17.5 percent by weight of grain syrup solids which contain at least approximately 50 percent by weight of dextrans;

approximately 2.5 to 17.5 percent by weight of grain syrup solids which contain at least 50 percent by weight of maltose;

approximately 3 to 12 percent by weight of an oil containing at least approximately 20 percent by weight of oleic acid, the oil being selected from a group consisting of olive oil, canola oil, sunflower oil, safflower oil and peanut oil;

approximately 1 to 11 percent by weight of medium chain triglycerides which contain in their fatty acid portion fatty acids having approximately 8 to 14 carbon atoms;

a nutritionally acceptable soluble magnesium salt which is substantially equivalent in magnesium content to 0.01 to 0.06 per cent by weight of magnesium citrate;

a nutritionally acceptable buffering agent which is substantially equivalent in its buffering capacity to approximately 0.5 to 2.5 percent by weight of dipotassium phosphate;

a nutritionally acceptable soluble calcium salt which is substantially equivalent in calcium content to approximately 0.01 to 0.065 percent by weight of calcium citrate;

a nutritionally acceptable ascorbic acid derivative which is substantially equivalent to approximately 0.05 to 0.25 percent by weight of calcium ascorbate;

approximately 0.40 to 0.65 percent by weight of β carotene or a carotinoid mixture which is substantially equivalent in vitamin A activity to said quantity of β-carotene;

approximately 0.1 to 0.4 percent by weight of D-α-tocopherol or a nutritionally acceptable tocopherol derivative which is substantially equivalent in vitamin E activity to said quantity of D-α-tocopherol;

a nutritionally acceptable source of chromium containing chromium ions in the trivalent or hexavalent form, and which is substantially equivalent to approximately 0.04 to 0.12 percent by weight of chromium polynicotinate;

approximately 0.008 to 0.022 percent by weight of glutathione;

approximately 0.08 to 0.22 percent by weight of N-acetylcysteine;

approximately 0.08 to 0.22 percent by weight of L-lysine hydrochloride, L-lysine or a nutritionally acceptable salt of L-lysine in a quantity substantially equivalent to said quantity of L-lysine hydrochloride;

approximately 0.08 to 0.22 percent by weight of L-threonine, and approximately 0.08 to 0.22 percent by weight of L-cysteine.

DETAILED DESCRIPTION OF THE INVENTION

In accordance with the present invention a medical food is provided which is administered to a patient who suffers from metabolic poisoning, for a number of days as the sole, or as substantially the sole source of nutrition or caloric intake of the patient. The purpose of administering the dietary composition to patients is to stimulate certain enzymes of the body which when sufficiently active are capable of clearing from the body numerous accumulated undesirable non-end product metabolites and toxins. Sources of such non-end product metabolites and toxins may be environmental, such as exposure to environmental contaminants, poisons, allergy producing agents and chemicals (such as pesticide residues), toxic trace elements, certain drugs and pharmaceuticals, as well as excessive levels of other non-end product metabolites which are formed in biochemical reactions in the body during states of altered metabolism.

Indications for treatment of a patient with a medical food comprising solely or substantially the composition of the present invention include the following syndromes and diseases: fatigue, hypotonia, depression, lassitude, muscle weakness, insomnia, recurring bad dreams, intestinal complaints (myalgia), confusion, and functional nervous system problems. Medically diagnosing a patient as suffering from "metabolic poisoning" which is treatable with a medical food of the composition of the present invention, that is ruling out specific diseases or other causes of the above-mentioned and related symptoms and thereby ruling out alternative forms of treatment, requires medical diagnosis based on observation, and may require medical testing. To describe the process how such diagnosis is performed and medical testing conducted, would be beyond the scope of describing the present invention. Once it is established, however, that a patient suffers from metabolic poisoning, administration of the composition of the present invention may be recommended medically. As it is described in more detail below, experience has shown that administration of a medical food of the composition of the present invention significantly improves the physical and psychological well-being of patients, and that the human body's ability to enzymatically process undesirable metabolites and toxins is demonstrably enhanced as a result of treatment in accordance with the present invention.

It should be noted at the outset, that the composition of the present invention is generally designed to utilize ingredients which tend to have oligoantigenicity, or only very low tendency to cause allergies, which give rise only to minimal amount of toxic non-end product metabolites of the type which have a tendency to be retained in the body, to contain nutrients and substances which cause up-regulation of hepatic enzymes, to contain no cholesterol, to contain only low quantities of fatty acids of the type which can give rise to cholesterol, and to contain only very low quantity of sodium ions. The dietary composition of the present invention is not intended to cause weight loss, although moderate weight loss may occur while a patient maintains a diet of substantially nothing other than the composition of the present invention. The dietary composition of the present invention is also designed to provide substantially all nutrients and vitamins required by the human body, and thus to provide a substantially balanced diet.

The composition of the present invention includes approximately 45 to 65 percent by weight of a protein concentrate which can be a grain protein concentrate or a vegetable protein concentrate. Suitable protein concentrates are rice protein concentrate, corn protein concentrate, oat protein concentrate, barley protein concentrate, wheat protein concentrate, bean protein concentrate, pea protein concentrate, soy bean protein concentrate, and kidney bean protein concentrate. The preferred embodiment of the dietary composition of the present invention comprises 34 percent rice protein concentrate. This rice protein concentrate is derived from white rice and is fortified with certain amino acids, to wit: L-lysine, L-threonine and L-cysteine.

The dietary composition of the present invention includes approximately 2.5 to 17.5 percent by weight of grain syrup solids which contain at least approximately 50 percent (by weight) of dextran. Suitable grain syrup solids are rice syrup solids, barley syrup solids and corn syrup solids. The preferred embodiment of the dietary composition of the present invention contains 17.5 percent (by weight) of rice syrup solids.

Still another component of the dietary composition of the present invention is approximately 2.5 to 17.5 percent by weight of a grain syrup solid which contains at least 50 percent by weight of maltose. Suitable grain syrup solids for this purpose are rice syrup solids, corn syrup solids and barley syrup solids. The preferred embodiment contains approximately 17.5 percent by weight of rice syrup solids containing maltose.

The dietary composition of the present invention also includes an oil which contains at least approximately 20 percent (by weight) of oleic acid. Suitable oils for this purpose are olive, canola, sunflower, safflower and peanut oils. The specific preferred embodiment of the dietary composition includes 2 percent of safflower oil. (Here, as well as elsewhere in the present description percentages are given "by weight".)

As another important fat-containing component of the composition of the present invention, the composition contains approximately 1 to 11 percent of medium chain triglycerides, that is triglycerides which have fatty acid moieties having 8 to 14 carbon atoms. A suitable source for these fatty acid triglycerides is, for example, the oil derived from coconuts, and related tropical oils. In this regard it should be noted that whereas coconut oil is high in saturated long chain fatty acids, and is therefore considered undesirable because it promotes formation of cholesterol, the medium chain triglycerides derived from coconut oil do not give rise to cholesterol. The preferred embodiment of the composition of the invention contains 5 per cent of medium chain triglycerides.

The dietary composition of the present invention contains a nutritionally acceptable magnesium salt, as a source of magnesium. Such acceptable salts include magnesium citrate, magnesium acetate and magnesium ascorbate. The amount of magnesium in the composition corresponds, as far as magnesium ion content is concerned, to approximately 0.01 to 0.06 percent (by weight) of magnesium citrate. The preferred embodiment contains approximately 0.02 percent magnesium citrate.

Another component of the composition is dipotassium phosphate, a buffering agent which is present in approximately 0.5 to 2.5 percent, by weight. Other buffering agents, which are nutritionally acceptable, such as ammonium acetate and potassium acetate can also be used in a quantity which is substantially equivalent, as far as buffering capacity is concerned, to the above noted quantity of dipotassium phosphate. The preferred embodiment of the composition contains 1.0 percent (by weight) of dipotassium phosphate.

The composition of the present invention contains a source of calcium ions in the form of a nutritionally acceptable water soluble calcium salt, such as calcium citrate, calcium chloride, calcium acetate or calcium ascorbate. The quantity of calcium ions in the composition corresponds to approximately 0.01 to 0.065 percent of calcium citrate, and the preferred embodiment contains 0.03 percent (by weight) of calcium citrate.

The composition of the present invention also contains sources or precursors for vitamins A, C, and E. More specifically, the composition contains approximately 0.05 to 0.25 percent calcium ascorbate, or another ascorbic acid derivative or salt which is equivalent in its vitamin C-like activity to the above-noted quantity of calcium ascorbate. The preferred embodiment contains 0.10 percent (by weight) of calcium ascorbate which is preferably obtained from a commercial source under the ESTER C tradename. Approximately 0.40 to 0.65 percent (by weight) of β-carotene, or an equivalent amount of a natural carotinoid mixture is a source (or precursor) of vitamin A in the composition of the present invention. The preferred embodiment of the composition contains approximately 0.4 percent (by weight) of β-carotene. Approximately 0.1 to 0.4 percent of D-α-tocopherol, or a nutritionally acceptable derivative of tocoperol (such as tocopherol acetate or palmitate) having vitamin E activity in a quantity equivalent to the just-noted quantity of D-α-tocopherol, is a source of vitamin E in the composition of the present invention. The preferred embodiment contains approximately 0.2 percent of D-α-tocopherol.

The composition of the present invention contains chromium in trivalent or hexavalent form, in an amount which is substantially equivalent to approximately 0.04 to 0.12 percent (by weight) of chromium polynicotinate. Other suitable and nutritionally acceptable sources of chromium ions are sodium and potassium chromate. The preferred embodiment contains approximately 0.04 (by weight) of chromium polynicotinate, which is available under the tradename CROMEMATE GTF.

The composition of the present invention also contains approximately 0.008 to 0.012 percent (by weight) of gluthathione and approximately 0.08 to 0.22 percent (by weight) of N-acetyl cysteine. The preferred embodiment contains approximately 0.010 percent gluthathione, and approximately 0.10 percent N-acetylcysteine.

The amino acids L-lysine either as free acid, hydrochloride or other nutritionally acceptable salt, and approximately 0.08 to 0.22 percent (by weight) of L-threonine are also present in the composition. L-lysin is present in a quantity which is substantially equivalent to approximately 0.08 to 0.22 percent (by weight) of L-lysine hydrochloride. The preferred embodiment of the composition has approximately 0.10 percent L-lysine hyrochloride and approximately 0.10 percent L-threonine. Still another component of the dietary composition of the present invention is approximately 0.08 to 0.22 percent (by weight) of the amino acid L-cysteine. The preferred embodiment of the composition contains 0.10 percent of L-cysteine.

The above-noted components or ingredients of the composition of the present invention are considered essential, in the sense that the unique combination of these components results in a composition which, when taken as a sole source, or substantially sole source of nutrition for a time period of approximately 4 or more days, usually cause substantial increases in hepatic detoxifying enzyme activity resulting in clearance from the body of accumulated non-end product metabolites and toxins, as is evidenced by the marked improvement in the condition of patients who have received treatment in accordance with the invention, and by certain objective diagnostic tests as well. The following further additional ingredients or components of the composition render the composition a source of a substantially balanced diet, and are therefore considered important but not necessarily required for practicing the invention.

Thus, the dietary composition of the invention optionally includes a nutritionally acceptable zinc salt in a quantity which is substantially equivalent to approximately 0.08 to 0.22 per cent by weight of zinc methionate. Suitable zinc salts or derivatives are zinc oxide (ZnO) zinc chloride (ZnCl$_2$) and zinc acetate (Zn(OAc)$_2$). The preferred embodiment of the composition contains approximately 0.08 percent (by weight) of zinc methionate.

The composition of the present invention optionally also has a source of molybdenum in the form of a nutritionally acceptable molybdenum salt in a quantity which is substantially equivalent to approximately 0.18 to 0.35 percent by weight of molybdenum histidinate. Sodium molybdate is, for example, another nutritionally acceptable molybdenum salt. The preferred embodiment of the composition has approximately 0.20 percent molybdenum histidinate.

Another optional component of the composition is biotin, or a nutritionally acceptable salt of biotin which is substantially equivalent to approximately 0.0018 to 0.045 percent by weight of biotin bitartarate. The preferred embodiment of the composition includes approximately 0.0018 percent (by weight) of biotin bitartarate.

The composition of the present invention optionally includes a source of dietary iron in the form of a nutritionally acceptable iron salt, preferably approximately 0.018 to 0.045 per cent by weight ferrous fumarate, or other ferrous salt (such as ferrous sulfate or ferrous chloride) which is equivalent in its iron content to the above-noted quantity of ferrous fumarate. The preferred embodiment of the invention contains approximately 0.018 percent (by weight) of ferrous fumarate.

Another "trace" metal ion which is optionally included in the composition of the present invention, is manganese in the form of a nutritionally acceptable salt of divalent or pentavalent mangenese ions which is substantially equivalent in manganese content to approximately 0.018 to 0.055 percent by weight of manganous gluconate. The preferred embodiment has approximately 0.020 percent (by weight) of manganous gluconate.

Still another "trace" element optionally included in the composition of the present invention, is selenium, in any nutritionally acceptable form in a quantity which is substantially equivalent in selenium content to approximately 0.004 to 0.015 percent by weight of selenomethionine. Examples of nutritionally acceptable forms of selenium are, in addition to selenomethionine, sodium selenate (Na$_2$Se$_2$O$_8$), and sodium selenite (Na$_2$SeO$_3$). The preferred embodiment of the composition contains approximately 0.004 percent (by weight) selenomethionine.

The composition of the present invention optionally also includes approximately 0.004 to 0.012 percent by weight of niacinamide or an equivalent quantity of niacin. The preferred embodiment of the composition has approximately 0.006 percent (by weight) of niacinamide. The composition of the present invention is prepared by admixing the above-described ingredients.

The dietary composition of the present invention comprises a powder-like mixture, which is administered to patients mixed with water or mixed with fruit juice, depending on the patient's preference for osmolarity, taste, and desired intake of calories. Treatment with the composition of the invention requires administration of the composition for several days, as the sole source of nutrition, or as substantially the sole source of nutrition of a patient. At least approximately 4 days of treatment with the composition is usually necessary to achieve positive results in terms of activation of hepatic detoxification enzymes, and a typical and recommended course of treatment is as follows. During the first three days of the treatment the patient takes all his or her caloric intake (meals) in the form of the composition of the invention mixed with water or fruit juice (preferably not with citrus juice, because citrus juice is allergenic to many persons). During the first three days of treatment the patient preferably takes 5 meals (5 servings) of the composition of the invention. A typical serving of the composition is approximately 44 grams, and such a serving contains approximately 175 calories. During the following 3 to 4 days of treatment a patient takes a substantial portion of his or her caloric intake by taking the dietary composition of the invention, preferably in the form of three servings, which is supplemented by meals, preferably two meals, of food products which contain low or very low quantity of allergy-producing products, little sodium, cholesterol, or saturated fatty acids. Treatment with the composition of the present invention typically continues for a total of seven days, or until substantial improvement is attained in the patient's physical and mental condition. Experience with hundreds of patients who suffered from metabolic poisoning as manifested by the above-described symptoms or conditions, has demonstrated significant improvement of the patients' condition as a result of treatment in accordance with the present invention.

In addition to the clinical manifestation of improvement in patients' conditions, tests have proven that a patient's ability to metabolize toxic substances is markedly enhanced as a result of treatment in accordance with the present invention. Specifically, it is generally accepted in the art that liver function can be measured by such standard laboratory methods as "salivary caffeine clearance" which tests cytochrome P450 activity, and "urinary hippurate analysis" which tests for glycine conjugation. These tests are well known and accepted in the medical arts; the urinary hippurate analysis test is described for example in Clinical Chemistry—Principles and Technics Bioscience Labs 2nd Edition page 1005, Harper & Row publishers, 1974; and the salivary caffeine clearance test is described, for example, in an article titled "Overnight Salivary Caffeine Clearance: A Liver Function Test Suitable for Routine Use" by Gerhard Jost et al., Hepatology, Volume 7, pp 338–344, 1987.

Briefly summarized, in the urinary hippurate analysis test a subject is given an oral dose of sodium benzoate, and during the next approximate 4 hours urine samples are collected and the urine's hippuric acid content is measured. Hippuric acid is N-benzoyl-glycine, and is an end product metabolite of benzoic acid. Stated differently, conjugating benzoic acid with glycine and excreting the resulting hippuric acid in the urine is the body's mechanism of ridding itself of benzoic acid, and the rate of hippuric acid excretion reflects on the liver's ability to metabolize, conjugate, and excrete undesirable substances by conjugation with glycine (normal range 32–71 percent).

In the salivary caffeine clearance test, the human subject is orally administered a (harmless) dose of caffeine, thereafter samples of saliva are collected, and the salive's caffeine content is analyzed at different times. It has been established that the saliva's caffeine content reflects the persons's blood serum's content. The "half life" of the disappearance of the administered dose of caffeine in the subject's serum can be calculated from the foregoing measurements. A shorter half life, of course, means a faster, more active metabolism capable of ridding the body of caffeine, and is understood to be a measure of hepatic cytochrome P450 enzyme activity. (Normal range 4.5–8.8 hours.) Table 1 below shows the results of representative tests on twenty-five patients, who before treatment in accordance with the present invention had demonstrated reduced hepatic detoxification activity in both the urinary hippurate output and salivary caffeine clearance tests. The table indicates data for the patients who are identified by their initials in the column under the heading Subject. The results for each subject in both tests are provided in the respective column under the heading Before, and the results after a 21 day long therapy in accordance with the present invention are indicated in the respective columns under the heading After. The averages for the 25 patients for these data, as well as the changes in the test results before and after the treatment, are also indicated in Table 1. It should be noted in this regard that a shorter caffeine "half life" indicates improved cytochrome P450 activity, and a larger output of hippuric acid indicates improved ability of the liver to detoxify benzoic acid (and other substances) by conjugation with glycine.

TABLE 1

| Subject | Salivary Caffeine Clearance (Hrs/half life) | | | Urinary Hippurate Output (% Converted) | | |
|---------|--------|-------|------|--------|-------|-------|
|         | Before | After | △    | Before | After | △     |
| LR      | 7.4    | 7.2   | −0.2 | 12.5   | 27.0  | +14.5 |
| MM      | 8.2    | 6.4   | −1.8 | 13.4   | 22.1  | +8.7  |
| CR      | 6.8    | 5.2   | −1.6 | 21.2   | 40.4  | +19.2 |
| JB      | 10.4   | 5.4   | −5.0 | 16.7   | 15.2  | −1.5  |
| CB      | 6.2    | 5.8   | −0.4 | 22.4   | 37.1  | +14.7 |
| NM      | 5.4    | 1.7   | −3.7 | 12.9   | 16.9  | +4.0  |
| TB      | 8.1    | 2.6   | −5.5 | 16.7   | 27.1  | +10.4 |
| CL      | 9.4    | 3.4   | −6.0 | 30.4   | 40.4  | +10.0 |
| NN      | 7.2    | 7.4   | +0.2 | 19.7   | 26.7  | +7.0  |
| SB      | 6.4    | 6.0   | −0.4 | 22.6   | 37.4  | +14.8 |
| BC      | 5.8    | 1.6   | −4.2 | 14.0   | 17.1  | +2.9  |
| AN      | 7.2    | 6.4   | −0.8 | 15.7   | 18.2  | +2.5  |
| MC      | 8.9    | 4.7   | −4.2 | 27.6   | 46.7  | +19.1 |
| LH      | 6.2    | 2.2   | −4.0 | 14.4   | 22.1  | +7.7  |
| RC      | 7.4    | 5.4   | −2.0 | 29.4   | 30.4  | +1.0  |
| MC      | 8.4    | 6.2   | −2.0 | 13.2   | 16.7  | +3.5  |
| DH      | 9.3    | 7.4   | −1.9 | 18.4   | 19.4  | ±1.0  |
| DM      | 6.2    | 5.8   | −0.4 | 24.5   | 30.7  | +6.2  |
| BS      | 5.8    | 6.0   | +0.2 | 26.2   | 24.2  | −2.0  |
| SS      | 6.2    | 5.9   | −0.3 | 21.1   | 37.6  | 15.5  |
| MS      | 7.4    | 6.8   | −0.6 | 17.6   | 30.4  | +12.8 |
| SH      | 6.4    | 5.8   | −0.6 | 23.4   | 30.8  | +7.4  |
| MH      | 6.8    | 6.0   | −0.8 | 24.6   | 44.7  | +20.1 |
| BB      | 7.1    | 4.5   | −2.6 | 17.1   | 28.1  | +11.0 |
| DB      | 7.8    | 6.1   | −1.7 | 19.4   | 26.5  | +7.1  |
| Average | 6.8    | 5.1   | −1.9 | 19.8   | 28.6  | +7.9  |

Table 2 indicates the results of of the same two tests on twelwe patients who in a control study, were given a placebo meal replacement program similar in calories to the composition of the present invention, but of a different composition, in accordance with the prior art. These data demonstrate that treatment with the composition of the present invention results in a marked increase in hepatic detoxifying ability of the liver of the subjects treated with the present invention as contrasted to the placebo group.

TABLE 2

| Subject | Salivary Caffeine Clearance (Hrs/half life) | | | Urinary Hippurate Output (% Converted) | | |
|---|---|---|---|---|---|---|
| | Before | After | △ | Before | After | △ |
| MM | 8.2 | 8.1 | −0.1 | 23.4 | 24.1 | +0.7 |
| LM | 7.4 | 7.6 | +0.2 | 26.1 | 29.3 | +3.2 |
| PM | 6.9 | 6.7 | −0.2 | 19.7 | 21.6 | +1.9 |
| SN | 6.2 | 6.0 | −0.2 | 18.6 | 16.7 | −1.9 |
| TM | 7.4 | 7.0 | −0.4 | 33.1 | 30.1 | +3.0 |
| CC | 6.9 | 7.1 | +0.2 | 16.6 | 19.6 | +3.0 |
| DC | 8.6 | 6.9 | −2.3 | 24.5 | 27.5 | +3.0 |
| MS | 6.6 | 7.1 | +0.5 | 26.7 | 25.1 | −1.6 |
| SB | 8.4 | 6.7 | −1.7 | 17.9 | 20.1 | +2.2 |
| ML | 7.9 | 7.8 | −0.1 | 20.6 | 24.6 | +4.0 |
| AS | 5.8 | 6.4 | +0.6 | 24.7 | 25.0 | +0.3 |
| JB | 6.4 | 5.8 | −0.6 | 25.2 | 26.0 | +0.8 |
| Average | 7.2 | 6.9 | .3 | 23.1 | 24.1 | 1.6 |

The level of statistical difference between the two groups was at the p<0.01 confidence interval for both caffeine and hippurate. This means that the subjects with reduced hepatic detoxification ability who were treated with the present invention (versus the control (placebo) group that received a dietical calorie and nutritionally balanced treatment) had a marked improvement in their ability to process and excrete endo and exotoxins by way of hepatic cytochrome P450 enzyme systems and hepatic conjugase enzymes.

The average reduction in caffeine clearance in the treatment group was 1.9 hours versus an increase in caffeine clearance of 0.3 hours in the control group. This illustrates a substantially significant increase in hepatic cytochrome P450 activity in the group treated with the invention versus the placebo group.

The average increase in hippurate excretion was 7.9 percent in the treatment group versus 1.6 percent in the control group. This indicates a statistically significant increase in hepatic glycine conjugation in the group treated with the invention versus the placebo.

The increase in hepatic detoxification ability in the treatment group is consistent with considerable clinical improvement in symptoms as measured by a screening questionnaire. The screening questionnaire is a modification of the well accepted Cornell Medical Index (CMI) which has been adapted specifically to evaluate the signs and symptoms of exo and endotoxicity. Total point scores in excess of 75 are considered clinically relevant as it relates to hepatic detoxification reduced activity or excess toxic body burden. Total symptom points on this metabolic clearance screening questionnaire used on patients in connection with the present invention were less then 50 percent of their initial values in patients treated with the invention and much improved versus those treated with the placebo as shown in Table 3.

TABLE 3

Clinical Improvement Before and After Treatment (Average Values)

| Group | Number of Subjects | Initial Symptoms (Points) | After Treatment | Difference |
|---|---|---|---|---|
| Treatment | 25 | 111 | 48 | 63 |
| Placebo | 12 | 120 | 105 | 15 |

Conclusion: A four fold reduction of clinical symptoms associated with toxicity in the treatment group versus the controls.

What is claimed is:

1. A composition designed for nutrition and metabolic detoxifixation of the human consumer of the product, the product comprising:

approximately 45 to 65 percent by weight of a protein concentrate selected from a group consisting of grain protein concentrate and vegetable protein concentrate;

approximately 2.5 to 17.5 percent by weight of grain syrup solids which contain at least approximately 50 percent by weight of dextran;

approximately 2.5 to 17.5 percent by weight of grain syrup solids which contain at least 50 percent by weight of maltose;

approximately 3 to 12 percent by weight of an oil containing at least approximately 20 percent by weight of oleic acid, the oil being selected from a group consisting of olive oil, canola oil, sunflower oil, safflower oil and peanut oil;

approximately 1 to 11 percent by weight of medium chain triglycerides which contain in their fatty acid portion fatty acids having approximately 8 to 14 carbon atoms;

a nutritionally acceptable soluble magnesium salt which is substantially equivalent in magnesium content to 0.01 to 0.06 percent by weight of magnesium citrate;

a nutritionally acceptable buffering agent which is substantially equivalent in its buffering capacity to approximately 0.5 to 2.5 percent by weight of dipotassium phosphate;

a nutritionally acceptable soluble calcium salt which is substantially equivalent in calcium content to approximately 0.01 to 0.065 percent by weight of calcium citrate;

a nutritionally acceptable ascorbic acid derivative which is substantially equivalent to approximately 0.05 to 0.25 percent by weight of calcium ascorbate;

approximately 0.40 to 0.65 percent by weight of β carotene or a carotinoid mixture which is substantially equivalent in vitamin A activity to said quantity of β carotene;

approximately 0.1 to 0.4 percent by weight of D-α-tocopherol or a nutritionally acceptable tocopherol derivative which is substantially equivalent in vitamin E activity to said quantity of D-α-tocopherol;

a nutritionally acceptable source of chromium containing chromium ions in the trivalent or hexavalent form, and which is substantially equivalent to approximately 0.04 to 0.12 percent by weight of chromium polynicotinate;

approximately 0.008 to 0.022 percent by weight of glutathione;

approximately 0.08 to 0.22 percent by weight of N-acetylcysteine;

approximately 0.08 to 0.22 percent by weight of L-lysine hydrochloride, L-lysine or a nutritionally acceptable salt of L-lysine in a quantity substantially equivalent to said quantity of L-lysine hydrochloride;

approximately 0.08 to 0.22 percent by weight of L-threonine;

approximately 0.08 to 0.22 percent by weight of L-cysteine, and a nutritionally acceptable zinc salt in a quantity which is substantially equivalent to approximately 0.08 to 0.22 percent by weight of zinc methionate.

2. The composition according to claim 1 further comprising a nutritionally acceptable molybdenium salt in a quantity which is substantially equivalent to approximately 0.18 to 0.35 percent by weight of molybdenum histidinate.

3. The composition according to claim 1 further comprising biotin or a nutritionally acceptable salt of biotin which is substantially equivalent to approximately 0.0018 to 0.045 percent by weight of biotin bitartarate.

4. The composition according to claim 1 further comprising a nutritionally acceptable salt of iron which is equivalent in iron content to approximately 0.018 to 0.045 percent by weight ferrous fumarate.

5. The composition according to claim 1 further comprising a nutritionally acceptable salt of divalent or pentavalent manganese ions which is substantially equivalent in manganese content to approximately 0.018 to 0.055 percent by weight of manganous gluconate.

6. The composition according to claim 1 further comprising a nutritionally acceptable source of selenium which is substantially equivalent in selenium content to approximately 0.004 to 0.015 percent by weight of selenomethionine.

7. The composition according to claim 1 further comprising approximately 0.004 to 0.012 percent by weight niacinamide or niacin in substantially equivalent quantity to said quantity of niacinamide.

8. A composition designed for nutrition and metabolic detoxifixation of the human consumer of the product, the product comprising:

approximately 45 to 65 percent by weight of a protein concentrate selected from a group consisting of rice protein concentrate, corn protein concentrate, oat protein concentrate, barley protein concentrate, wheat protein concentrate, bean protein concentrate, pea protein concentrate, soybean protein concentrate, and kidney bean protein concentrate;

approximately 2.5 to 17.5 percent by weight of grain syrup solids which contain at least approximately 50 percent by weight of dextran, the grain syrup solids being selected from a group consisting of rice syrup solids, barley syrup solids and corn syrup solids;

approximately 2.5 to 17.5 percent by weight of grain syrup solids which contain at least 50 percent by weight of maltose, the grain syrup solids being selected from a group consisting of rice syrup solids, corn syrup solids and barley syrup solids;

approximately 3 to 12 percent by weight of an oil containing at least approximately 20 percent by weight of oleic acid, the oil being selected from a group consisting of olive oil, canola oil, sunflower oil, safflower oil and peanut oil;

approximately 1 to 11 percent by weight of medium chain triglycerides which contain in their fatty acid portion fatty acids having approximately 8 to 14 carbon atoms;

a nutritionally acceptable soluble magnesium salt which is substantially equivalent in magnesium content to 0.01 to 0.06 per cent by weight of magnesium citrate, said magnesium salt being selected from a group consisting of magnesium citrate, magnesium acetate and magnesium ascorbate;

a nutritionally acceptable buffering agent which is substantially equivalent in its buffering capacity to approximately 0.5 to 2.5 percent by weight of dipotassium phosphate, the buffering agent being selected from a group consisting of dipotassium phosphate, ammonium acetate and potassium acetate;

a nutritionally acceptable soluble calcium salt which is substantially equivalent in calcium content to approximately 0.01 to 0.065 percent by weight of calcium citrate, the calcium salt being selected from a group consisting of calcium citrate, calcium chloride, calcium acetate and calcium ascorbate;

a nutritionally acceptable ascorbic acid derivative which is substantially equivalent to approximately 0.05 to 0.25 percent by weight of calcium ascorbate, the ascorbic acid derivative being selected from a group consisting of ascorbic acid, sodium ascorbate, calcium ascorbate and potassium ascorbate;

approximately 0.40 to 0.65 percent by weight of $\beta$ carotene or a carotinoid mixture which is substantially equivalent in vitamin A activity to said quantity of $\beta$ carotene;

approximately 0.1 to 0.4 percent by weight of D-$\alpha$-tocopherol or a nutritionally acceptable tocopherol derivative which is substantially equivalent in vitamin E activity to said quantity of D-$\alpha$-tocopherol;

a nutritionally acceptable source of chromium containing chromium ions in the trivalent or hexavalent form, and which is substantially equivalent to approximately 0.04 to 0.12 percent by weight of chromium polynicotinate, the source of chromium being selected from a group consisting of chromium polynicotinate, potassium chromate and sodium chromate;

approximately 0.008 to 0.022 percent by weight of glutathione;

approximately 0.08 to 0.22 percent by weight of N-acetylcysteine;

approximately 0.08 to 0.22 percent by weight of L-lysine hydrochloride, L-lysine or a nutritionally acceptable salt of L-lysine in a quantity substantially equivalent to said quantity of L-lysine hydrochloride;

approximately 0.08 to 0.22 percent by weight of L-threonine;

approximately 0.08 to 0.22 percent by weight of L-cysteine;

a nutritionally acceptable zinc salt in a quantity which is substantially equivalent to approximately 0.08 to 0.22 percent by weight of zinc methionate;

a nutritionally acceptable molybdenium salt in a quantity which is substantially equivalent to approximately 0.18 to 0.35 percent by weight of molybdenum histidinate;

biotin or a nutritionally acceptable salt of biotin which is substantially equivalent to approximately 0.0018 to 0.045 percent by weight of biotin bitartarate;

a nutritionally acceptable salt of iron which is equivalent in iron content to approximately 0.018 to 0.045 percent by weight ferrous fumarate;

a nutritionally acceptable salt of divalent or pentavalent mangenese ions which is substantially equivalent in manganese content to approximately 0.018 to 0.055 percent by weight of manganous gluconate;

a nutritionally acceptable source of selenium which is substantially equivalent in selenium content to approximately 0.004 to 0.015 percent by weight of selenomethionine, and approximately 0.004 to 0.012 percent by weight niacinamide or niacin in substantially equivalent quantity to said quantity of niacinamide.

9. A process for metabolically detoxifying a human being, by administering to said human being for a time period not less than approximately 4 days a diet, a substantial portion of which is a composition which comprises:

approximately 45 to 65 percent by weight of a protein concentrate selected from a group consisting of grain protein concentrate and vegetable protein concentrate;

approximately 2.5 to 17.5 percent by weight of grain syrup solids which contain at least approximately 50 percent by weight of dextran;

approximately 2.5 to 17.5 percent by weight of grain syrup solids which contain at least 50 percent by weight of maltose;

approximately 3 to 12 percent by weight of an oil containing at least approximately 20 percent by weight of oleic acid, the oil being selected from a group consisting of olive oil, canola oil, sunflower oil, safflower oil and peanut oil;

approximately 1 to 11 percent by weight of medium chain triglycerides which contain in their fatty acid portion fatty acids having approximately 8 to 14 carbon atoms;

a nutritionally acceptable soluble magnesium salt which is substantially equivalent in magnesium content to 0.01 to 0.06 percent by weight of magnesium citrate;

a nutritionally acceptable buffering agent which is substantially equivalent in its buffering capacity to approximately 0.5 to 2.5 percent by weight of dipotassium phosphate;

a nutritionally acceptable soluble calcium salt which is substantially equivalent in calcium content to approximately 0.01 to 0.065 percent by weight of calcium citrate;

a nutritionally acceptable ascorbic acid derivative which is substantially equivalent to approximately 0.05 to 0.25 percent by weight of calcium ascorbate;

approximately 0.40 to 0.65 percent by weight of β carotene or a carotenoid mixture which is substantially equivalent in vitamin A activity to said quantity of β carotene;

approximately 0.1 to 0.4 percent by weight of D-α-tocopherol or a nutritionally acceptable tocopherol derivative which is substantially equivalent in vitamin E activity to said quantity of D-α-tocopherol;

a nutritionally acceptable source of chromium containing chromium ions in the trivalent or hexavalent form, and which is substantially equivalent to approximately 0.04 to 0.12 percent by weight of chromium polynicotinate;

approximately 0.008 to 0.022 percent by weight of glutathione, approximately 0.08 to 0.22 percent by weight of N-acetylcysteine;

approximately 0.08 to 0.22 percent by weight of L-lysine hydrochloride, L-lysine or a nutritionally acceptable salt of L-lysine in a quantity substantially equivalent to said quantity of L-lysine hydrochloride;

approximately 0.08 to 0.22 percent by weight of L-threonine, and approximately 0.08 to 0.22 percent by weight of L-cysteine.

10. The process in accordance with claim 9 wherein the composition administered in the process further comprises:

a nutritionally acceptable zinc salt in a quantity which is substantially equivalent to approximately 0.08 to 0.22 percent by weight of zinc methionate;

a nutritionally acceptable molybdenium salt in a quantity which is substantially equivalent to approximately 0.18 to 0.35 percent by weight of molybdenum histidinate;

biotin or a nutritionally acceptable salt of biotin which is substantially equivalent to approximately 0.0018 to 0.045 percent by weight of biotin bitartarate;

a nutritionally acceptable salt of iron which is equivalent in iron content to approximately 0.018 to 0.045 percent by weight ferrous fumarate;

a nutritionally acceptable salt of divalent or pentavalent mangenese ions which is substantially equivalent in manganese content to approximately 0.018 to 0.055 percent by weight of manganous gluconate;

a nutritionally acceptable source of selenium which is substantially equivalent in selenium content to approximately 0.004 to 0.015 percent by weight of selenomethionine, and approximately 0.004 to 0.012 percent by weight niacinamide or niacin in substantially equivalent quantity to said quantity of niacinamide.

11. The process in accordance with claim 9 wherein in the composition which is administered to the human being:

the protein concentrate is rice protein concentrate;

the grain syrup solids which contain at least approximately 50 percent by weight of dextran are rice syrup solids, and the grain syrup solids which contain at least 50 percent by weight of maltose are rice syrup solids.

12. The process in accordance with claim 9 wherein in the composition which is administered to the human being:

the oil containing at least approximately 20 percent by weight of oleic acid is safflower oil.

* * * * *